(12) United States Patent
Turkki et al.

(10) Patent No.: US 11,932,843 B2
(45) Date of Patent: Mar. 19, 2024

(54) ADHERENT CELL CULTURE SUBSTRATE SAMPLING DEVICE

(71) Applicant: Trizell Ltd., Chinnor (GB)

(72) Inventors: Vesa Turkki, Kuopio (FI); Nigel Parker, Chinnor (GB)

(73) Assignee: TRIZELL LTD., Chinnor (GB)

( * ) Notice: Subject to any disclaimer, the term of this patent is extended or adjusted under 35 U.S.C. 154(b) by 1027 days.

(21) Appl. No.: 15/763,123

(22) PCT Filed: Nov. 9, 2017

(86) PCT No.: PCT/IB2017/057008
§ 371 (c)(1),
(2) Date: Mar. 26, 2018

(87) PCT Pub. No.: WO2018/087690
PCT Pub. Date: May 17, 2018

(65) Prior Publication Data
US 2020/0172847 A1    Jun. 4, 2020

Related U.S. Application Data

(60) Provisional application No. 62/419,613, filed on Nov. 9, 2016.

(51) Int. Cl.
| | | |
|---|---|---|
| *C12M 1/12* | (2006.01) | |
| *C12M 1/00* | (2006.01) | |
| *C12M 3/00* | (2006.01) | |
| *C12N 5/00* | (2006.01) | |

(52) U.S. Cl.
CPC ............ *C12M 37/04* (2013.01); *C12M 21/08* (2013.01); *C12M 23/14* (2013.01); *C12M 23/28* (2013.01); *C12M 25/00* (2013.01); *C12M 25/02* (2013.01); *C12M 29/00* (2013.01); *C12N 5/0068* (2013.01)

(58) Field of Classification Search
CPC ...... C12M 21/08; C12M 23/14; C12M 23/28; C12M 25/00; C12M 25/02; C12M 25/14; C12M 29/00; C12M 33/00; C12M 33/04; C12M 37/04; C12N 5/0068
See application file for complete search history.

(56) References Cited

U.S. PATENT DOCUMENTS

| | | | |
|---|---|---|---|
| 5,601,757 A | 2/1997 | Biselli et al. | |
| 10,851,341 B2 | 12/2020 | Kasuto et al. | |
| 2005/0101008 A1 | 5/2005 | Diresta | |
| 2010/0099127 A1 | 3/2010 | Bodner | |
| 2010/0248370 A1* | 9/2010 | Moynahan | B01L 3/0275 |
| | | | 435/286.1 |
| 2012/0052565 A1* | 3/2012 | DeRosa | C08J 7/02 |
| | | | 435/305.1 |
| 2013/0071872 A1 | 3/2013 | Ho et al. | |
| 2014/0170644 A1 | 6/2014 | Hadayer et al. | |
| 2017/0114315 A1* | 4/2017 | Yokoo | C12M 23/48 |

FOREIGN PATENT DOCUMENTS

| | | |
|---|---|---|
| CN | 102994377 A | 3/2013 |
| CN | 103476924 A | 12/2013 |
| EP | 1637584 A1 | 3/2006 |
| KR | 10-2005-0017761 A | 2/2005 |
| RU | 130077 U1 | 7/2013 |
| SU | 1682858 A1 | 10/1991 |
| WO | WO-01/008630 A2 | 2/2001 |
| WO | WO-2005/124310 A1 | 12/2005 |
| WO | WO2016091744 A1 | 6/2016 |
| WO | WO-2018/087690 A1 | 5/2018 |

OTHER PUBLICATIONS

Merten, Otto-Wilhelm. "Manufacturing of viral vectors for gene therapy: part I. Upstream processing." Future Science. Pharm. Bioprocess. 2014. 2(2). 183-203.
International Search Report for PCT/IB2017/057008, 3 pages (dated Jan. 26, 2018).
Written Opinion for PCT/IB2017/057008, 5 pages (dated Jan. 26, 2018).
Hanna P. Lesch, et al., Process Development of Adenoviral Vector Production in Fixed Bed Bioreactor: From Bench to Commercial Scale. Human Gene Therapy. Aug. 2015. 560-571. Published Online: Jul. 14, 2015 https://doi.org/10.1089/hum.2015.081.

* cited by examiner

*Primary Examiner* — Blaine Lankford
(74) *Attorney, Agent, or Firm* — Casimir Jones SC; Lisa Mueller (57) ABSTRACT

A device for aseptically obtaining a physical sample of an adherent cell culture substrate from an adherent cell culture bioreactor. This enables the operator to directly evaluate e.g., cell density/confluence on the substrate without contaminating the cell culture.

14 Claims, 6 Drawing Sheets

ADHERENT CELL CULTURE SUBSTRATE SAMPLING DEVICE

RELATED APPLICATIONS

This application claims priority from U.S. provisional patent filing Ser. No. 62/419,613, filed 9 Nov. 2016, the contents of which are here incorporated by reference.

GOVERNMENT INTEREST

None

PRIOR PUBLIC DISCLOSURES

None

JOINT RESEARCH AGREEMENTS

Not applicable

BACKGROUND

The art teaches large scale cell culture using either suspended or adherent cell culture. See generally Merten, Otto-Wilhelm et al., *Manufacturing Of Viral Vectors For Gene Therapy: Part I—Upstream Processing*, 2 *Pharmaceutical Bioprocessing* 183-203 (2014). Suspended cell culture entails, for example, culturing cells free floating in the liquid cell culture medium. Alternatively, one can culture cells attached to micro-beads which in turn float free in the medium. For the purposes of this patent, I use the term "suspended" cell culture to encompass both of these cell culture approaches.

Alternatively, one can culture cells attached to a solid substrate which is so bulky or dense that it does not suspend freely in the cell culture medium. Such substrates include, for example, packed synthetic fibers. Alternatively, one can use paper-like sheets of fibers, perhaps cut into smaller pieces.

Industrially-consistent cell culture often requires sampling the cell culture from time to time, to obtain samples of the cells for analysis. Obtaining a sample from a suspended cell culture is relatively easy. Because the cells (either alone or on a micro-bead) are suspended in the liquid culture medium, one need merely take a sample of the culture medium with the cells suspended in it. This can be done via a bioreactor sampling port using a pipette.

In contrast, where the cells are cultured as adherent to a non-suspended cell culture substrate, using a pipette obtains a sample of the liquid cell culture medium, but not of the substrate on which the cells adhere. One thus can assess the culture medium for metabolites from the cell culture, but one cannot directly examine the cultured cells.

The art teaches to obtain samples of adherent cells by adding protease to the cell culture medium. This removes adherent cells from the substrate, so the cells float freely in the liquid medium. One can thus use a pipette to draw a sample of the culture medium, and obtain a sample of the cells. Protease, however, perturbs the cell culture. Further, protease-released cells fail to provide certain important information, including e.g., how confluent the cells were when adhered to the solid substrate. Thus, protease provides an effective way to remove adherent cells after one is finished culturing them, but protease is not an acceptable way to remove samples of adherent cells during the adherent culture process.

The art thus needs a way to take a sample of cells adhered to a non-suspended substrate in an adherent cell culture system, where one can take the sample of cells without significantly perturbing or altering the remaining (non-sampled) cells.

I have developed a simple solution. It is easy to manufacture. It nonetheless preserves the aseptic environment even in large-scale and commercial-scale adherent bioreactors. (In this patent, I use the term "aseptic" to mean free of undesired microorganisms.)

BRIEF DESCRIPTION

My apparatus includes an aseptic sampling container or housing such as a sterile sampling tube, aseptically connected to a port on a bioreactor cell culture vessel. The vessel contains cell culture medium and a solid adherent cell culture substrate. The aseptic housing contains a device for obtaining a sample of the cell culture substrate with adherent cells attached. The aseptic housing is then sealed and removed from the cell culture vessel, so that the vessel remains aseptically contained even after the aseptic housing is removed. The adherent cells on the cell culture substrate sample contained in the aseptic housing may then be analyzed.

DETAILED DESCRIPTION

Bioreactors, fermentors and tissues culture containers are herein referred as bioreactors. Bioreactors provide suitable growth conditions for variety of cultured microorganisms, herein referred as cells. In most occasions one wants to grow only specific types of cells in the bioreactor and growth of any other cells such as bacteria is highly unwanted. Therefore complex procedures are applied to keep the bioreactors and all used solutions free of contaminating cells from the environment.

An adherent cell culture bioreactor vessel contains liquid cell culture medium and in that liquid medium, a solid substrate providing a surface on which cultured cells can adhere and grow. This provides a closed aseptic environment for adherent cell culture.

The art teaches a variety of suitable solid substrates able to provide a solid support onto which cultured cells can adhere. The substrate is typically a fiber because fibers are inexpensive and uniform, and provide a high ratio of surface area to volume. The art teaches that the fiber can be polymer fiber, for example a polyester or polypropylene fiber. Other fibers such as silicate or lactate electrospun nanofibers may also be used. The substrate may be used as packed or loose fibers.

The substrate may alternatively be a sheet. Substrate sheets may be monolithic. Sheets also can be made from fibers, much as a sheet of paper is made from cellulose fibers. A variety of adherent cell culture substrates and "fixed-bed" carriers are known in the art. In my invention, these are largely-interchangeable equivalents.

Sampling of bioreactors for cell count and analysis is of utmost importance in bioprocessing. Aseptic sampling of cells (or carriers on top of which cells grow) in fixed bed bioreactors has to-date generally known to be difficult or impossible. See Merten et al. (2014), supra. Cell growth has thus been followed and estimated by using a biomass probe, or by measuring nutrient consumption or metabolite by-products dissolved in the liquid culture medium. Cell distribution on the substrate carrier, however, has remained an unknown variable. Thus, cell confluence, and indeed the adherent cells themselves, have not been able to be further analyzed.

This is a significant problem for certain types of cell culture. For example, in plasmid transfection, the local cell density or confluence is a major determinant of transfection efficacy and efficiency. In lieu of actual confluence observations, the art teaches to use a calculated average cell number. The average number, however, may not accurately describe the actual growth pattern of the cells. Locally, the cells may grow in tight clumps in one area, while being entirely absent from another, instead of being spread evenly.

There thus is a need in the art for a way to sample the solid substrate of carrier on which the cells adhere. This would allow for more efficient process optimization. It would make possible, for example, a precise analysis of transfection efficacy, by showing how well the transfection mixture has been internalized by cells, and where. Also, this would make possible the use of a number of cell-based assays, like proteomic and gene-expression analyses. The lack of cell sampling options from fixed bed bioreactors has thus been a significant drawback in industrial-scale bioprocessing.

I have found a solution which is simple, cost-effective and accurate. My invention may perhaps be most easily understood by looking at FIG. 1.

Figure 1:
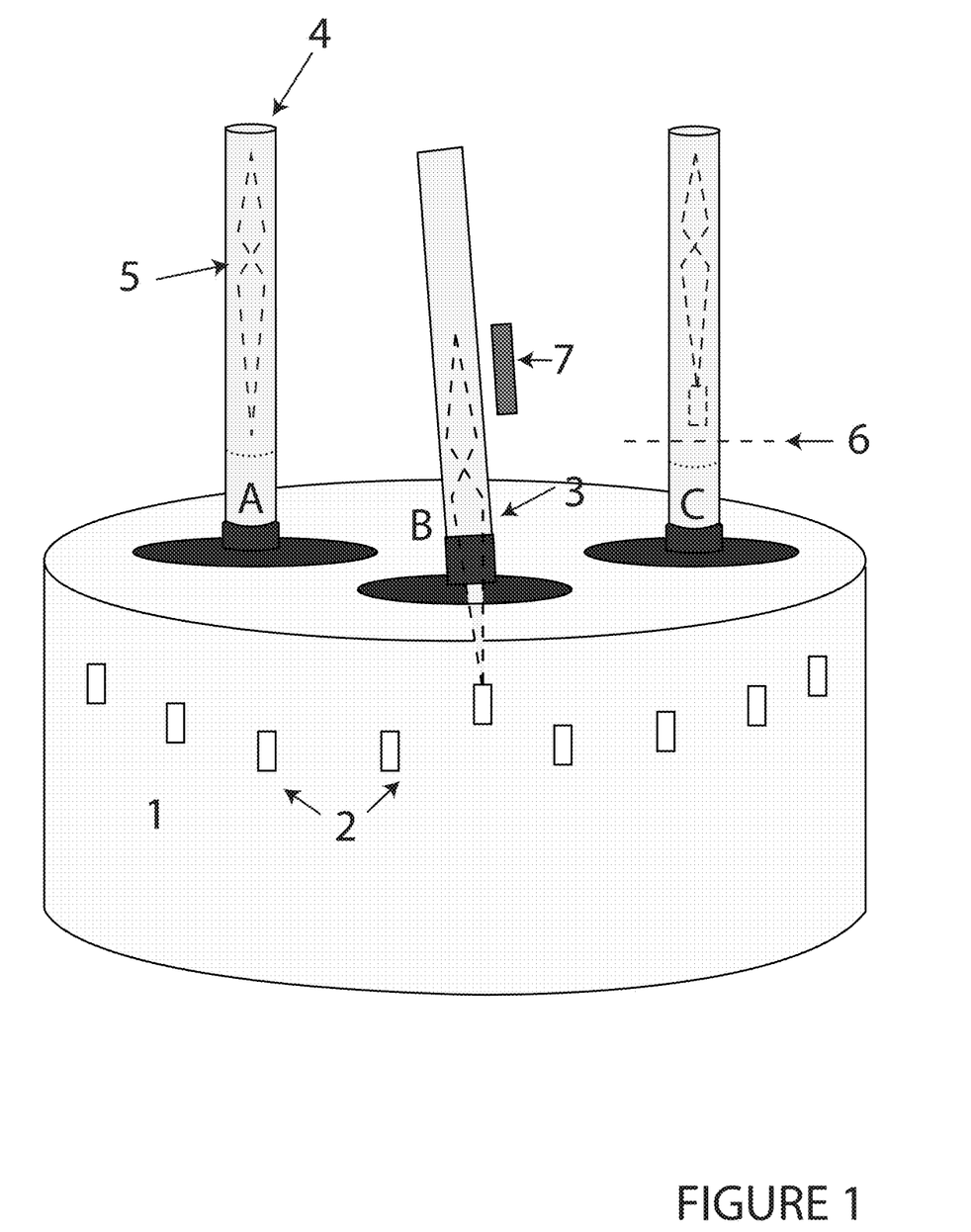
FIG. 1 illustrates a version of my sampling device, tweezers housed aseptically in a bioreactor sampling tube, and illustrates its method of use.

FIG. 1 illustrates the structure and temporal operation of one example of my invention. FIG. 1 shows an adherent-culture bioreactor vessel [1] filled with liquid cell culture media. In this liquid media is a solid cell culture substrate [2] (FIG. 1 shows small strips of fiber sheets). The bioreactor vessel [1] bears one or more aseptic ports [3]. Commercially-available bioreactors typically have several ports to allow input on fresh media, output of used media, input of fresh oxygen or other gas etc.

Figure 2:
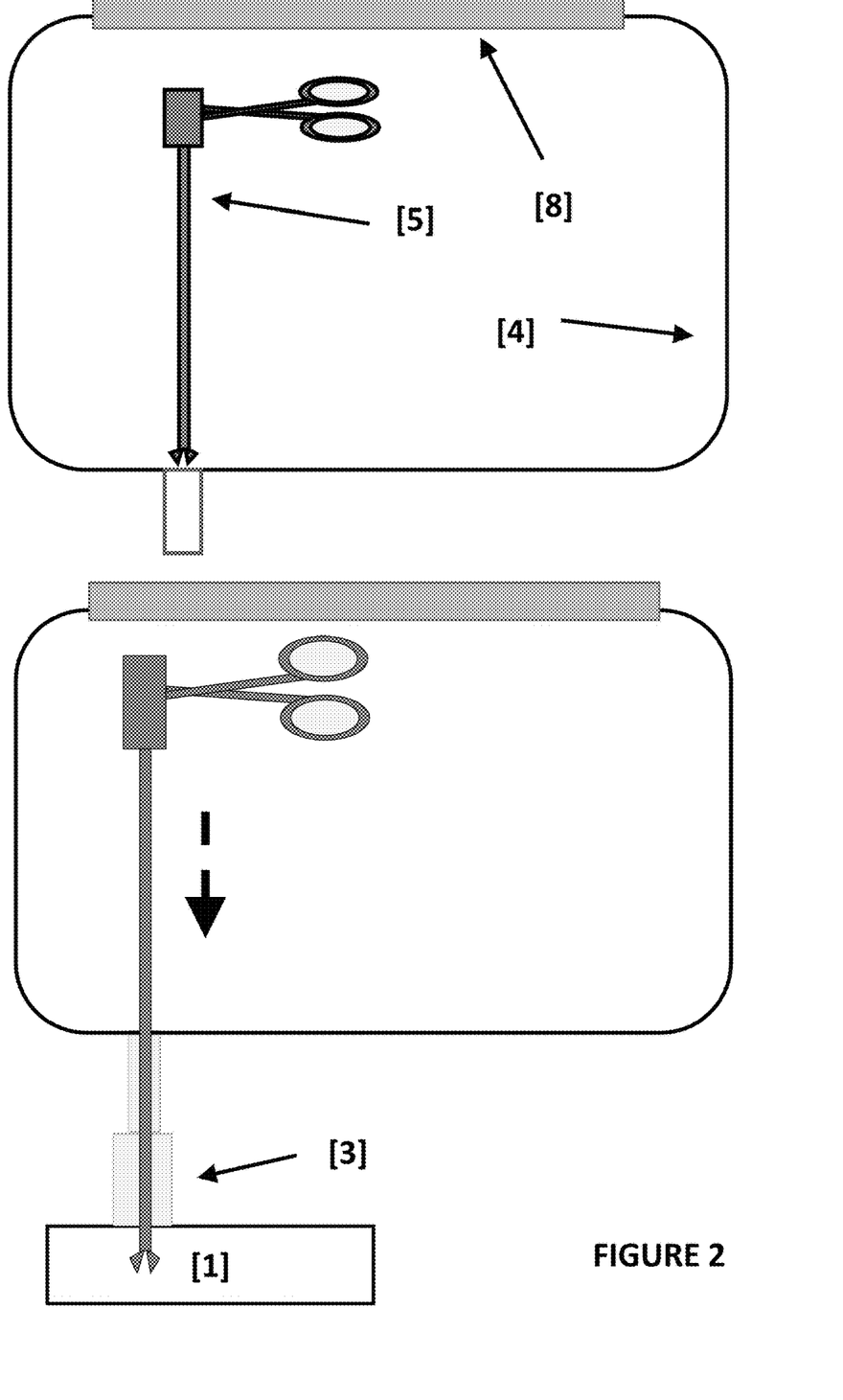
FIG. 2 illustrates another version of my sampling device, forceps housed aseptically in a sterile sampling bag.

At least one port is aseptically connected to a sampling device housing [4]. As illustrated in FIG. 1, the sampling device housing is a flexible tube. One may alternatively use a sterile bag as shown in FIG. 2, having a sealable end [8] into which one can load the sampling device [5], e.g., forceps, into the bag and then aseptically seal the bag [4]. Alternatively, one may for example use a rigid plastic or glass tube.

The sampling device housing [4] contains a solid substrate sampling device [5] able to obtain a sample of the solid substrate for adherent cell culture [2]. For example, FIG. 1 illustrates tweezers. FIG. 2 alternatively illustrates forceps. One may alternatively use a rod with a fish-hook type hook on the end. Alternatively, one can use a suction device able to obtain a sample of the solid substrate for adherent cell culture.

If tweezers or forceps are used, I prefer the housing [4] be flexible enough to enable an operator to manually manipulate the tweezers or forceps simply by manipulating the housing. If the a solid substrate sampling device [5] is ferrous metal, then one can use a magnet [7] to move the sampling device [5] within the housing [4].

The housing [4] can be sealed to separate it from the bioreactor. If so, then I prefer the seal on the housing end connected to the bioreactor be easily openable to enable an operator to move the tweezers from that opening. It is of note that the housing [4] can comprise a bag which allows extended space for manipulation of large tools such as cutting forceps (FIG. 2).

To make my device, one can assemble the housing [4], place the sampling device [5] in it, seal the assembly and then sterilize the assembly by e.g., autoclaving or radiation. The sterilized sealed housing [4] with sampling device [5] can then be aseptically attached to a bioreactor port [3]. This can be a standard port provided on a standard commercially-available version of a bioreactor. Alternatively, one can add to a bioreactor a new port(s) specifically for substrate sampling. So doing enables the operator to continue to use the pre-existing standard ports for their intended uses, as culture medium in- and out-puts, gas input etc. I prefer to provide several ports because this enables the ports to be permanently sealed after use, minimizing contamination risk. Alternatively, one can re-use the same port [3] several times.

FIG. 1 also illustrates the method of taking a solid substrate sample. To take a substrate sample, one begins with a housing [4] attached to a port [A]. One then opens the port [B] (if needed) and then passes the sampling device through the opened port [B], to access the bioreactor interior containing the solid cell culture substrate [2]. This manipulation may be done with the aid of a magnet [7]. One then obtains a sample of solid cell culture substrate [2] using the sampling device [5]; if tweezers in a flexible tube is used, then one can do this simply by compressing the flexible tube to manipulate the tweezers. The sampling device [5] holding the solid cell culture substrate [2] sample are then returned into the housing via the open port [C] by e.g., using a magnet or manipulating the housing. The housing is then sealed from the bioreactor [6]. The sampling device [5] may then be removed from the housing [4] without contaminating the bioreactor [1].

Biosafety is an important aspect of this invention. Once the housing [4] is sealed [6] from the bioreactor [1], then the portion of the housing [4] containing the sampling device [5] and the sample [2] can be entirely detached from the port [3] and transported into a laminar flow hood and opened there, enabling aseptic removal of the sample [2]. The sampled material is not therefore openly handled in the laboratory. This avoids open handling of the sampled material and the accompanying risk of contamination. Further, open handling of samples is not allowed if the material in bioreactor poses a health risk to operators.

During a clinical manufacturing run, where the bioreactor is making a biological product for human use, no antibiotics can be used in the cell culture media, no hatch is permitted in the bioreactor casing, and good manufacturing practices prohibit opening the bioreactor. My invention thus started with my facing these constraints, and trying to figure out how to get more insight into what was happening in the adherent cell culture in the bioreactor without being able to open the bioreactor, nor to use antibiotics in the media to prevent inadvertent contamination. I thus began working on this with the idea of using the existing ports in a commercially-available bioreactor casing to sample the reactor substrate in sterile manner. However, these same principles apply to a custom-made bioreactor with an additional port(s) specifically intended to be used for substrate sampling. My idea in general is to provide a mechanism to aseptically take samples of solid cell culture substrate, without perturbing the viability of the entire cell culture.

Given my basic idea, one can easily make other equivalent versions. For example, one could use a barbed metal rod in lieu of tweezers, where the barbs would catch and retain a fiberous substrate sample. The barb could be raised and lowered by an external magnet. Alternatively, the housing could be a flexible plastic sheet or bag, where the operator could manually hold the distal end of the rod through the plastic, manipulating the rod as desired.

In certain bioreactors carriers are immobilized inside a doughnut shaped basket. On top of the carrier layer there are mesh and a top grid, which compresses the carrier mass into the basket. However there is an opening between the basket wall and the top grid, from where the carrier bed could be sampled using the tweezer or wire approaches described above. In case no such opening is available, one could use cutting tweezers to create an opening for carrier sampling. In this application it is especially practical if the sampling device housing is a bag assembly consisting of tube and a bag as described in FIG. 2.

Example 1

Figure 3:
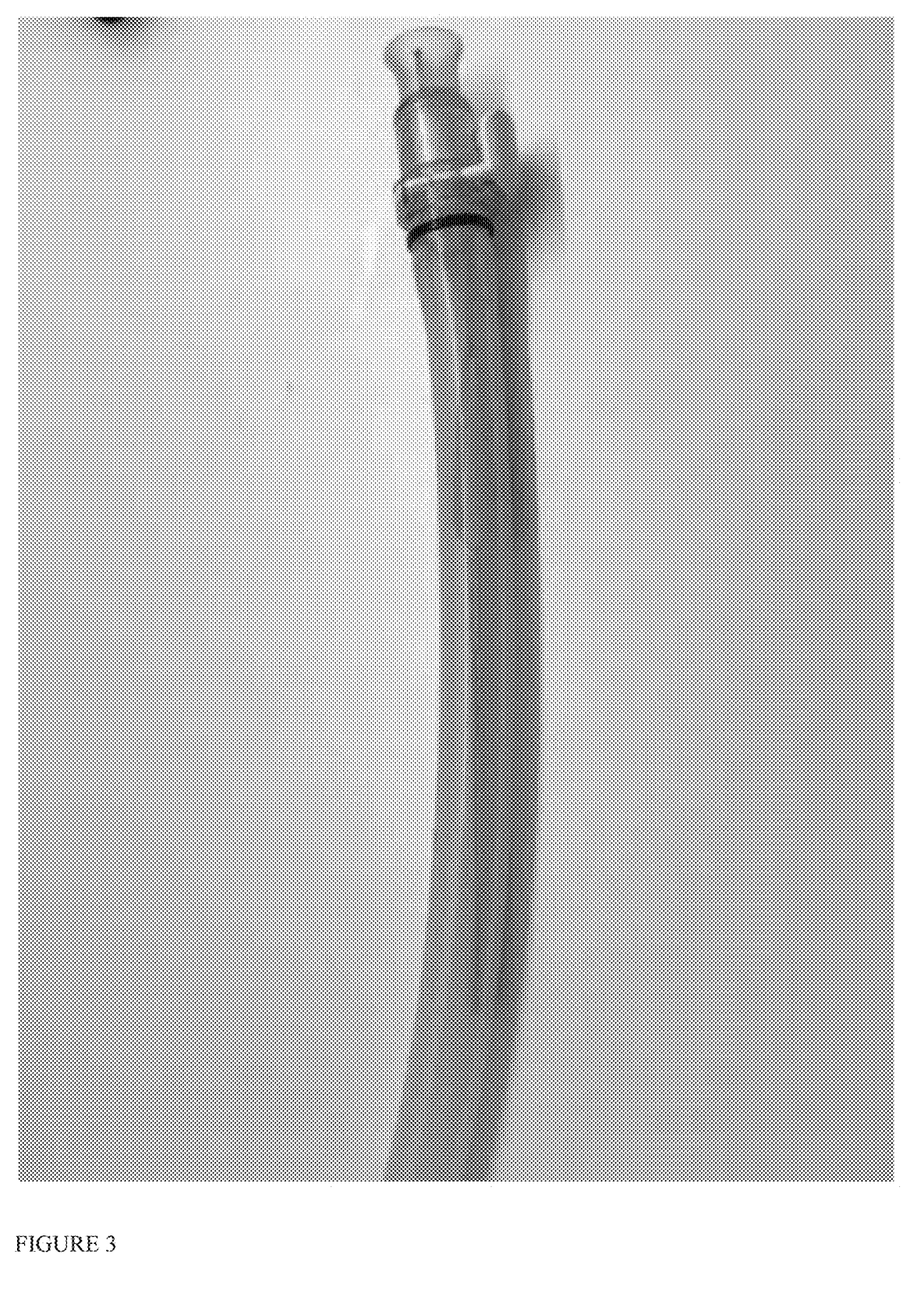
FIG. 3 is a photograph of an example if tweezers housed in a sampling tube per FIG. 1.

To test my apparatus, I evaluated it in a standard iCELLis™ 500 single-use bioreactor. I provide photographs of this work as FIGS. 3-6. During the preparative phase of the sampling, a sampling device (in this example tweezers) is inserted, sampling tip first, into the first end of a sampling device housing with corresponding diameter to the bioreactor port. This is shown in FIG. 3. I used a ¾" tube to fit the ¾" Gas-Out port. In this example, I used an adapter (an MPX adapter) placed to the first end of the tube. The second end of the tube can be sealed, or an adapter can be placed into the second end. I then autoclaved this sampling apparatus with suitable caps to fit the adapters (in this case, MPX caps to fit onto the MPX adapters). After I autoclaved the apparatus, I used the MPX caps to close the housing in an aseptic manner, inside a laminar flow hood.

Figure 4:
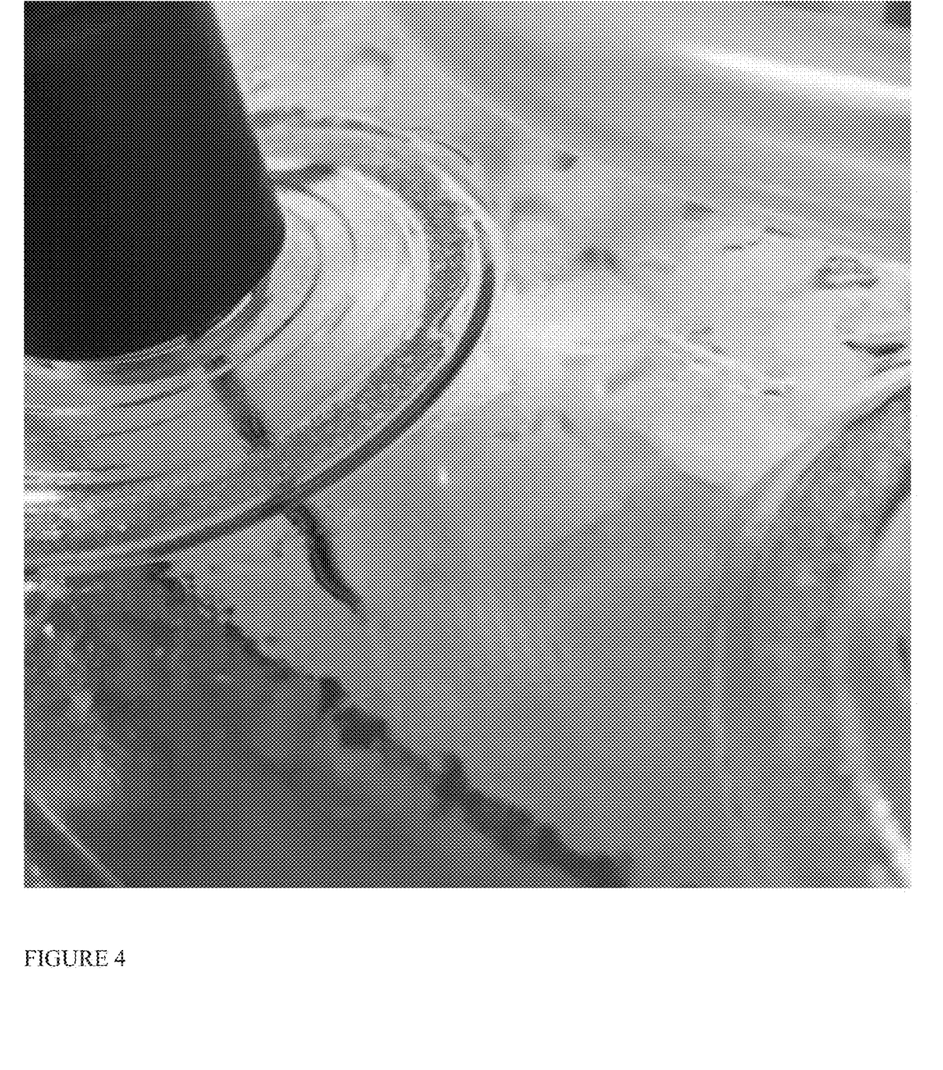
FIG. 4 is a photograph showing the tweezers being inserted into the bioreactor vessel to access and obtain solid cell culture substrate.
Figure 5:
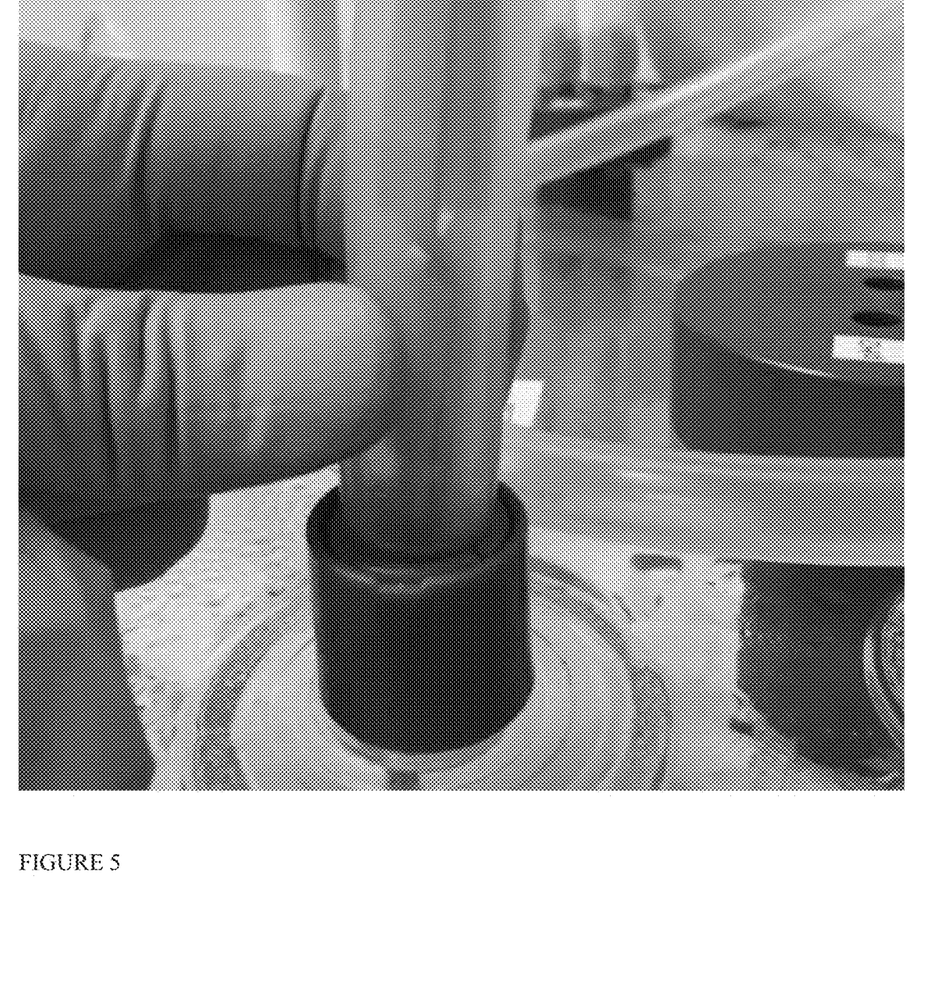
FIG. 5 is a photograph showing an operator manipulating the tweezers housed in the sampling tube.
Figure 6:
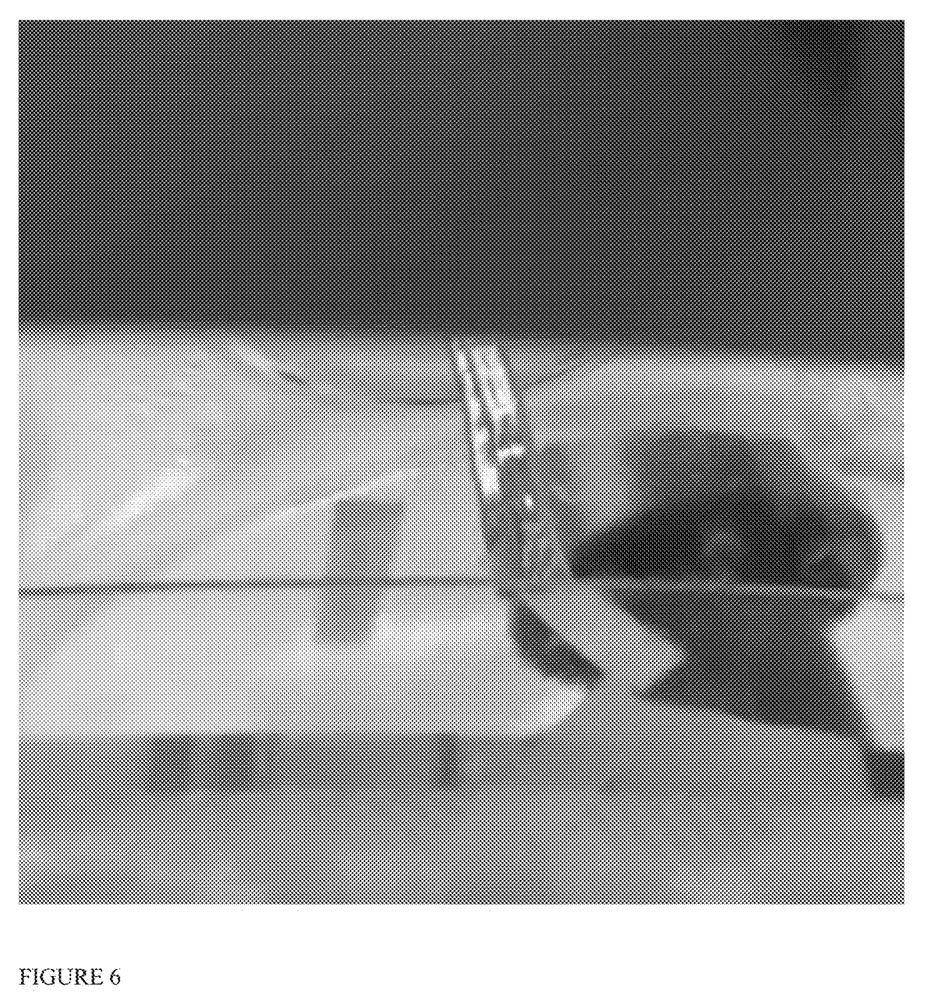
FIG. 6 is a photograph showing the tweezers obtaining a piece of solid cell culture substrate from a bioreactor.

At the time of the sampling, I stopped the gas flow into the reactors for the duration of the sampling. The second end of the sampling device housing is then welded into the Gas-Out port. Then the sampling device is slid downwards through the tube into the port. This is shown in FIG. 4. With the iCELLis™ 500 bioreactor, the sampling device can then be guided though an opening between fixed bed basket and the top grid of the bioreactor, so that the sampling device can grab a carrier, or several carriers, from the fixed bed. A strong magnet may be used to help the process. Grease or ethanol may be sprayed into the carrier container to reduce friction, unless those are seen detrimental to the process. Use of a thin, flexible material on the sampling device container enables the operator to manually manipulate the tweezers inside the container. This is shown in FIG. 5. Successfully obtaining a piece of the adherent cell culture substrate is demonstrated in FIG. 6.

The sampling device together with the carrier/substrate it is holding are then together removed so that the sampled material and the sampling device are removed from the bioreactor and into the housing. In this example, I provided a housing with long enough tubing for welding the original tube back. Basically, it is beneficial to retract the sampling device back into the original sample device housing. The tube is then sealed and/or a new tube is welded into the gas out line.

As an end result, the tweezers and the sampled carriers can be closed or sealed into the sampling device holder tube in aseptic manner. The structure of my apparatus enables one to do this without biosafety risk to the operator, nor the risk of contaminating the reactor.

The sampling device housing tube can then be transported to and opened in a laminar flow hood for carrier sample preparation and analysis.

We claim:

1. An adherent cell culture bioreactor comprising:
   a bioreactor container having a bioreactor container wall defining a bioreactor container exterior and a bioreactor container interior, the bioreactor container interior able to aseptically contain liquid cell culture media and a solid substrate for adherent cell culture,
   a port disposed through the bioreactor container wall to enable communication between the bioreactor container exterior and the bioreactor container interior,
   a sampling device housing aseptically connected to the port, wherein the sampling device housing comprises a sampling device housing exterior and a sampling device housing interior, wherein the sampling device housing is disposed on the port so that the sampling device housing interior can be in aseptic communication with the bioreactor container interior, and
   a solid substrate sampling device contained within the sampling device housing in the sampling device housing interior,
   wherein at least a portion of the sampling device can be passed from the sample device housing interior through the port into the bioreactor container interior to aseptically obtain a sample of solid substrate contained in the bioreactor container interior.

2. The bioreactor of claim 1, wherein the sampling device is selected from the group consisting of tweezers, forceps, suction device and hook.

3. The bioreactor of claim 2, wherein the sampling device housing comprises a tube and the sampling device comprises tweezers.

4. The bioreactor of claim 2, wherein the sampling device housing comprises a bag and the sampling device comprises foreign body forceps.

5. The bioreactor of claim 1, further comprising a magnet disposed on the exterior of the sampling device housing, the magnet able to manipulate the sampling device disposed in the interior of the sampling device housing.

6. The bioreactor of claim 1, further comprising a membrane disposed between the bioreactor container interior and the sampling device housing interior.

7. The bioreactor of claim 1, wherein the sampling device housing can be aseptically detached from the port.

8. A method for aseptically taking a sample of an adherent cell culture substrate, the method comprising:
   obtaining the bioreactor of claim 1, the bioreactor container interior aseptically containing liquid cell culture media and a solid substrate for adherent cell culture, and then
   using the sampling device to aseptically obtain a sample of the solid substrate for adherent cell culture.

9. A method for aseptically taking a sample of an adherent cell culture substrate, the method comprising:

obtaining the bioreactor of claim 7, the bioreactor container interior aseptically containing liquid cell culture media and a solid substrate for adherent cell culture, and then using the sampling device to aseptically obtain a sample of the solid substrate for adherent cell culture, and then aseptically detaching the sampling device housing from the port.

10. A method for producing a cell culture product, the method comprising:

obtaining the bioreactor of claim 1, the bioreactor container interior aseptically containing liquid cell culture media and a solid substrate for adherent cell culture, and then culturing a cell culture in the liquid cell culture media, and then using the sampling device to aseptically obtain a sample of the solid substrate for adherent cell culture, and then analyzing the sample to confirm the presence of the cell culture product.

11. A method for producing a cell culture product, the method comprising:

obtaining the bioreactor of claim 7, the bioreactor container interior aseptically containing liquid cell culture media and a solid substrate for adherent cell culture, and then culturing a cell culture in the liquid cell culture media, and then using the sampling device to aseptically obtain a sample of the solid substrate for adherent cell culture, and then analyzing the sample to confirm the presence of the cell culture product.

12. The bioreactor of claim 2, wherein the sampling device comprises a suction device.

13. The bioreactor of claim 1, wherein the sampling device housing is a flexible tube or a sterile bag having a sealable end.

14. The bioreactor of claim 1, further comprising aseptically withdrawing the sampling device and the sample from the bioreactor container interior via the port to return the sampling device and the sample to the sampling device housing interior.

* * * * *